(12) United States Patent
Peri et al.

(10) Patent No.: US 7,442,763 B2
(45) Date of Patent: Oct. 28, 2008

(54) COMPOSITIONS FOR TREATING ABNORMALITIES IN GLOMERULAR FILTRATION, PATENT DUCTUS ARTERIOSUS AND OSTEOPOROSIS

(75) Inventors: Krishna G. Peri, St-Laurent (CA); Sylvain Chemtob, Montréal (CA)

(73) Assignee: Hopital Sainte-Justine, Quebec (CA)

( * ) Notice: Subject to any disclaimer, the term of this patent is extended or adjusted under 35 U.S.C. 154(b) by 869 days.

(21) Appl. No.: 10/162,004

(22) Filed: Jun. 4, 2002

(65) Prior Publication Data
US 2003/0017988 A1    Jan. 23, 2003

Related U.S. Application Data

(63) Continuation of application No. PCT/CA00/01445, filed on Dec. 6, 2000, which is a continuation-in-part of application No. 09/455,483, filed on Dec. 6, 1999, now abandoned.

(51) Int. Cl.
*A61K 38/04*  (2006.01)
*A61K 38/00*  (2006.01)

(52) U.S. Cl. .............................. 530/329; 530/328; 514/2

(58) Field of Classification Search ........................ None
See application file for complete search history.

(56) References Cited

U.S. PATENT DOCUMENTS

| | | | |
|---|---|---|---|
| 5,508,384 A | 4/1996 | Murphy et al. | |
| 5,605,814 A | 2/1997 | Abramovitz et al. | |
| 5,759,789 A | 6/1998 | Abramovitz et al. | |
| 5,955,575 A | 9/1999 | Peri et al. | |
| 6,300,312 B1 | 10/2001 | Chemtob et al. | |
| 6,984,719 B1 | 1/2006 | Chemtob et al. | |
| 2003/0017988 A1 | 1/2003 | Peri et al. | |
| 2004/0235749 A1 | 11/2004 | Chemtob et al. | |

FOREIGN PATENT DOCUMENTS

| | | | |
|---|---|---|---|
| WO | WO 92/04450 | * | 3/1992 |
| WO | WO 94/20127 | | 9/1994 |
| WO | WO 95/00551 | | 1/1995 |
| WO | WO 95/11987 | | 5/1995 |
| WO | WO 95/29193 | | 11/1995 |
| WO | WO 96/06856 | | 3/1996 |
| WO | WO 96/19233 | | 6/1996 |
| WO | WO 96/23225 | | 8/1996 |
| WO | WO 97/12624 | | 4/1997 |
| WO | WO 97/18236 | | 5/1997 |
| WO | WO 97/34621 | | 9/1997 |
| WO | WO 98/10651 | * | 3/1998 |
| WO | WO 98/26070 | | 6/1998 |
| WO | WO 99/55849 | | 11/1999 |

OTHER PUBLICATIONS

Schramm et al. "The Inhibition of Human Immunodeficiency Virus Proteases By Interface Peptides", 1996, Antiviral Research, vol. 30. pp. 155-170.*

Schramm, H.J., The inhibition of human immunodeficiency virus proteases by 'interface peptides', Antiviral Research, 1996, vol. 30 No. 2,3:155-70.

Ichikawa, A., etal., Molecular aspects of the structures and functions of the prostaglandin E receptors, 1996, J. Lipid Mediators Cell Signalling: 14: 83-87.

Bastien, Y.,etal., Cloning, Functional Expression, and Characterization of the Human Prostaglandin $E_2$ Subtype*, 1994, J. Biol.Chem. 269 (16): 11873-77.

Bhattacharya, M.,etal., Developmental Changes in Prostaglandin $E_2$ Receptor Subtypes in Porcine Ductus Arteriosus, 1999, Circulation. 100: 1751-56.

Nguyen,M., etal.,The prostaglandin receptor $EP_4$ triggers remodelling of the cardiovascular system at birth, 1997, Nature. 390: 78-81.

Segi, E., etal.,Patent Ductus Arteriosus and Neonatal Death in Prostaglandin Receptor EP4-Deficient Mice, 1998,Biochemical and Biophysical Research Comm. 246: 7-12.

Breyer, M.D., etal., Regulation of renal function by prostaglandin E receptors, 1998, Kidney Int. 54 (Supple.67): S88-94.

Morath, R.,etal. Immunolocalization of the Four Prostaglandin $E_2$ Receptor Proteins EP1, EP2, EP3, and EP4 in Human Kidney, 1999, J.Am.Soc.Nephrol. 10: 1851-60.

Breyer, M.D., etal., Differential localization of prostaglandin E receptor subtypes in human kidney, 1998, Am.J.Physiol. 270: F912-918.

Scholondoff, D. etal.,Prostaglandins and other arachidonic acid metabolites in the kidney, 1986, Kidney Int. 29: 108-19.

Friedlander,G., etal., $PGE_2$ Binding Sites and PG-Stimulated Cyclic AMP Accumulation in Rat Isolated Glomeruli and Glomerular Cultured Cells, 1983, Mol. Cell. Endocrinol. 30: 201-214.

Sugimoto, Y.,etal., Distinct cellular localization of mRNAs for three subtypes of prostaglandin E receptor in Kidney, 1994, American Physiological Society, F823-G828.

Tai, H.,etal., Transcriptional Induction of Cyclooxygenase-2 in Osteoblasts Is Involved in Interleukin-6-Induced Osteoclast Formation*, 1997, Endocrinology, 138: 2372-2379.

(Continued)

*Primary Examiner*—Cecilia Tsang
*Assistant Examiner*—Maury Audet
(74) *Attorney, Agent, or Firm*—Klauber & Jackson (57) ABSTRACT

The present invention relates to a composition of matter comprising novel prostaglandin E2 receptor antagonists, and their use in treatments for regulating the fluid filtration in the kidney, preventing bone mineral loss in osteoporosis and dental disease and additionally, closure of ductus arteriosus (DA) in premature infants or fetal animals. Additionally, the compositions include linear peptides, peptide analogs, and peptidomimetics.

5 Claims, 3 Drawing Sheets

OTHER PUBLICATIONS

Narumiya, S, etal., Prostanoid Receptors: Structures, Properties, and Functions, 1999, Physiol. Rev. 79: 1193-1226.

Merrifield, R.B., Solid Phase Peptide Synthesis, Stewart & Young, W h Freeman Co., San Francisco, 1969, 2149-2154.

Arban, D., etal., Regulation of prostanoid vasomotor effects and receptors in choroidal vessels of newborn pigs, 1997, Am.J. Physiol. 272: R995-1001.

Teyssier, G., etal., Real-Time Cross-Sectional Ultrasonographic Imaging of the Newborn Lamb Heart. Technical Aspects, 1989, J. Cardiovascular Technol. 8: 259-266.

Rudinger, J., Characteristics of the amino acids as components of a peptide hormone sequence. In Peptide Hormones, Ed. By JA Parsons. University Park Press, pp. 1-7, 1976, Lofts, F.J., etal., Specific short transmembrane sequences can inhibit transformation by the mutant neu growth factor receptor in vitro in vivo, Oncogene 8: 2813-2820, 1993.

Wise, H., etal, Activation of the Prostaglandin EP4-Receptor Subtype is Highly Coupled to Inhibition of N-Formyl-Methionyl-Leucyl-Phenylalanine Stimulated Rat Neutrophil Aggregation Prostaglandins, Leukotriens and Essential Fatty Acids, Vo. 58, 1998, pp. 77-84.

Abramovitz, M., etal., Cloning and Expression of a cDNA for the Human Prostanoid FP Receptor, 1994, Journal of Biol. Chem., vol. 269, No. 4, pp. 2632-2636.

Coleman, RA.,etal., VIII. International Union of Pharmacology Classification of Prostanoid Receptors: Properties, Distribution, and Structure of the Receptors and Their Subtypes, 1994, Pharmacological Reviews, vol. 46, No. 2, pp. 205-229.

Crankshaw DJ., etal., Effects of some naturally occurring prostanoids and some cycloxygenase inhibitors on the contractility of the human lower uterine segment in vitro[1], 1994, Can J Physiol Pharmacol 72: pp. 870-874.

Griffin, BW., etal., AL-8810: A Novel Prostaglandin $F_{2a}$ Analog with Selective Antagonist Effects at the Prostaglandin $F_{2a}$ (FP) Receptor, 1999, Journal of Pharmacology and Experimental Therapeutics, vol. 290, No. 3, pp. 1278-1284.

Li, D. etal., Inhibition of Prostaglandin Synthesis in Newvorn Pigs Increases Cerebral Microvessel Prostaglandin $F_{2a}$ and Prostaglandin $E_2$ Receptors, Their Second Messengers and Vasoconstrictor Response to Adult Levels, 1996, The Journal of Pharmacology and Experimental Therapeutics, vol. 278, No. 1, pp. 370-377.

Li, D. etal., Key role for cyclooxygenase-2 in $PGE_2$ and $PGF_{2a}$ receptor regulation and cerebral blood flow of the newborn, 1997, The American Physiological Society, pp. R1283-R1290.

Lumsden, MA., etal., Is Prostaglandin $F_2$ Involved In The Increased Myometrial Contractility Of Primary Dysmenorrhoea?, 1983, Prostaglandins 25(5); pp. 683-692.

Novy, MJ., etal., Role of Prostaglandins, Prostacyclin, and Thromboxanes in the Physiologic Control of the uterus and in Parturition, 1980, Seminars in Perinatology 4: pp. 45-66.

Powell, AM., etal., Menstrual-$PGF_{2a}$ And $TXA_2$ In Normal and Dysemnorrheic Women and Their Temporal Relationship to Dysemenorrhea[1], 1985, Prostaglandins vol. 29, No. 2., pp. 273-289.

Strader CD., etal., Structure and Function of G Protein-Coupled Receptors, 1994, Annu. Rev. Biochem. 63: pp. 101-132.

Taylor,JM, etal., Peptides As Probes For G Protein Signal Transduction, 1994, Cell Signal 6: pp. 841-849.

\* cited by examiner

COMPOSITIONS FOR TREATING ABNORMALITIES IN GLOMERULAR FILTRATION, PATENT DUCTUS ARTERIOSUS AND OSTEOPOROSIS

CROSS REFERENCE TO RELATED APPLICATIONS

The present application is a continuation of International Application PCT/CA00/01445, filed Dec. 6, 2000, which in turn, is a continuation-in-part of U.S. patent application Ser. No. 09/455,483, filed Dec. 6, 1999 now abandoned by the inventors herein. All of the foregoing applications are incorporated by reference in their entirety.

BACKGROUND OF THE INVENTION (a) Field of the Invention

The invention relates to compounds and the use of novel peptide and peptidomimetic antagonists of a G protein coupled receptor, in treatments focused on regulating the fluid filtration in the kidney in case of acute renal failure, end stage renal disease, glomerulonephritis and other nephropathies, on decreasing resorption and bone mineral loss as in osteoporosis and dental diseases and additionally, closure of ductus arteriosus (DA) in premature infants or fetal animals.

(b) Description of Prior Art

Prostaglandins are derived from the oxygenation of arachidonic acid by prostaglandin (PG) synthases. Prostaglandins mediate a wide variety of physiological actions, such as vasomotricity, sleep/wake cycle, intestinal secretion, lipolysis, glomerular filtration, mast cell degranulation, neurotransmission, platelet aggregation, leuteolysis, myometrial contraction and labor, inflammation and arthritis, patent ductus arteriosus, cell growth and differentiation. Prostanoids mediate their actions through binding to distinct receptors which belong to the super family of rhodopsin-like seven transmembrane helical receptors. These receptors are coupled to heterotrimeric G-proteins comprising of $\alpha, \beta$ and $\gamma$ subunits which, upon activation, elicit alterations in cell calcium, initiate phosphoinositide hydrolysis or promotion or repression of cyclic adenosine monophosphate synthesis.

Of the five pharmacologically-distinct prostanoid receptors for $PGE_2$, $PGI_2$, $PGD_2$, $PGF_{2\alpha}$ and $TxA_2$, four subtypes of $PGE_2$ receptor are described (Ichikawa, et al. 1996). These are $EP_1$, $EP_2$, $EP_3$ which has several splice variants and $EP_4$. Cloned human $EP_4$ (also known as prostaglandin E2 receptor subtype EP4) is a 488 amino acid glycoprotein, linked to $G_{\alpha s}$ and involved in stimulation of adenylate cyclase and cAMP synthesis (Abramovitz, M. et al., U.S. Pat. Nos. 5,759,789 and 5,605,814). $EP_4$ receptor is expressed at a high level in intestine, but at much lower levels in lung, kidney, thymus, uterus and brain (Bastien, Y. et al. 1994 *J. Biol. Chem.* 269 (16):11873-77). $EP_4$ is expressed in ductus arteriosus (Bhattacharya, M. et al. 1999. *Circulation.* 100:1751-56). Paradoxically, $EP_4$ knock-out mice die after birth due to insufficient closure of ductus arteriosus (Nguyen, M. et al. 1997. *Nature.* 390:78-81; Segi, E. et al., 1998). Hence the mechanism of ductal patency and the role of $EP_4$ remain elusive.

$PGE_2$ is abundantly produced in kidney and is involved in the regulation of renal microcirculation, salt and water transport, renin release (Breyer, M. D. et al. 1998. *Kidney Int.* 54 (Suppl. 67): S88-94). All EP receptors have been shown to be regionally distributed in the kidney structures (Morath, R. et al. 1999. *J. Am. Soc. Nephrol.* 10: 1851-60) and are associated with specific functions. All studies on the distribution of EP receptors in kidney showed that $EP_4$ receptor is uniquely expressed in glomeruli (Breyer, M. D. et al. 1998. *Am. J. Physiol.* 270: F912-918; Morath, R., 1999), however the presence of this receptor in other structures of the nephron, such as collecting duct (Breyer, M. D., et al. 1998), the media of renal arteries and vasa recta (Morath, R. et al. 1999) is variously reported. $EP_4$ transcripts were also found in juxtaglomerular granule cells and is consistent with $PGE_2$-induced cAMP synthesis in these cells; hence $EP_4$ may also play a role in renin secretion. Glomerular prostaglandins are thought to affect filtration (Schlondoff, D. et al. 1986. *Kidney Int.* 29: 108-19) and renin release. $PGE_2$ increases cAMP levels in isolated glomeruli (Freidlander, G. et al., 1983. *Mol. Cell. Endocrinol.* 30: 201-214). It is suggested that $EP_4$ receptor coupled to cAMP synthesis may regulate glomerular filtration (Sugimoto, Y. et al., 1994), though a direct demonstration of its role is lacking. Most importantly, there is no data in the literature on whether stimulation or antagonism of EP4 receptor would result in increased glomerular filtration or how improving glomerular filtration could have therapeutic benefits in acute renal disease end stage renal disease, glomerulonephritis and diabetic nephropathy.

Bones undergo continuous remodeling in which bone formation is carried out by osteoblasts and bone resorption is carried out by osteoclasts. These processes are controlled by several humoral factors such as parathyroid hormone, estradiol, vitamin D, cytokines, growth factors and prostaglandins. It is known that osteoclast induction by interleukin-1 (IL-1) is inhibited by aspirin-like drugs (Tai, H., et al., 1997. *Endocrinology.* 138: 2372-2379). PGE2 analogs with EP4 receptor agonistic activity promoted osteoclast formation in cocultures of mouse osteoblasts and bone marrow cells and similar experiments using cells from EP4-knockout mice resulted in reduced osteoclast formation, suggesting a role for EP4 receptor in osteoclastogenesis in mice (cited in Narumiya, S. et al. 1999. *Physiol. Rev.* 79: 1193-1226). Hence it is expected that EP4 antagonists would have therapeutic benefits in medical conditions such as osteoporosis, dental diseases and other diseases where bone loss is integral part of the disease process. Lack of selective antagonists to EP4 receptor hindered progress in this area of research; it is therefore one of the objects of the present invention to overcome one or more of these deficiencies in the art.

It would be desirable to be provided with a prostaglandin E2 receptor subtype EP4 receptor antagonist capable of inhibiting at least one functional consequence of said receptor activity.

It would be desirable to be provided with a method of use for such an antagonist in a suitable pharmaceutical formulation with the purpose of improving glomerular filtration and/or urine output of a patient while treating end stage renal disease glomerulonephritis, diabetic nephropathy or acute renal failure, or closing ductus arteriosus (DA) in a premature infant patient, or preventing further bone loss in osteoporosis, dental disease, and other medical conditions where bone loss is a problem.

In order to further the search for small molecule antagonists of EP4 receptor using highthroughput screening approaches, it is desirable to provide a bioassay or a kit in which appropriately labelled antagonist of EP4 receptor of the present invention could be used as a ligand.

SUMMARY OF THE INVENTION

One aim of the present invention is to provide a peptidic or peptidomimetic form of a prostaglandin E2 receptor subtype EP4 antagonist capable of inhibiting at least one of the functional consequences the receptor activation.

Another aim of the invention is to provide a compound which comprises a peptide of the following general formula:

Y1-R1-R2-R3-R4-R5-R6-R7-R8-Z1 wherein,
Y1 is attached to the N-terminus of the peptide and selected from the group consisting of a proton, a sequence of 1-3 amino acids, or a blocking group such as a carbamate group, an acyl group composed of a hydrophobic moiety such as cyclohexyl, phenyl, benzyl, short chain linear and branched alkyl groups of 1-8 carbons of which acetyl and benzoyl are examples;
R1 is selected from the group consisting of Val, Ala, Ile, Gln, Leu, or Arg;
R2 is selected from the group consisting of Ala, Ile, Phe, Arg, or Leu;
R3 is selected from the group consisting of Pro, Thr, Ser, Tyr, Leu, or Val;
R4 is selected from the group consisting of Met, Ala, Gly, Ser, Val, or Ile;
R5 is selected from the group consisting of Thr, Pro, Tyr, Leu, Gly, or Gln;
R6 is selected from the group consisting of is Val, Cys, Ile, Gly, Glu, or Ser;
R7 is selected from the group consisting of is Pro, Val, Cys, Leu, Glu or Asn;
R8 is selected from the group consisting of is Ser, Leu, Thr, or Ala
Z1 is attached to the carboxy-terminus of the peptide and selected from the group consisting of proton, $NH_2$, 1-3 amino acids as well as arylalkyl amines such as benzylamine, phenylethylamine, phenylpropylamine, and aliphatic amines possessing short chain linear and branched alkyl groups of 1 to 8 carbons.

The invention also aims to provide a pharmaceutical composition containing a peptidic or peptidomimetic compound wherein said compound is capable of inhibiting at least one functional consequence of prostaglandin E2 receptor subtype EP4 activity.

As yet another objective is to disclose a compound wherein the compound comprises a peptide having a structural formula:

Y2-AA1-AA2-AA3-AA4-AA5-AA6-AA7-AA8-Z2 wherein:
Y2 is attached to the N-terminus of the peptide and selected from the group consisting of a proton, a sequence of 1-3 amino acids, or a blocking group such as a carbamate group, an acyl group composed of a hydrophobic moiety such as cyclohexyl, phenyl, benzyl, short chain linear and branched alkyl groups of 1-8 carbons of which acetyl and benzoyl are examples;
AA1 is selected from the group consisting of no residue, Ile, Leu, Phe and related alpha-amino acids possessing hydrophobic side-chains, arylalkyl amines such as benzylamine;
AA2 is selected from the group consisting of no residue, Leu, Ile, Phe and related alpha-amino acids possessing hydrophobic side-chains, arylalkyl amines such as benzylamine;
AA3 is selected from the group consisting of no residue, Ala, Ser, Thr and other related alpha amino acids possessing side chains containing hydroxyl or H-bond forming groups;
AA4 is selected from the group consisting of Ser, Thr, and related alpha-amino acids possessing side chains containing hydroxyl groups or H-bond forming groups;
AA5 is selected from the group consisting of Ala, Tyr, Phe, and other related alpha amino acids possessing side chains containing benzoyl and phenolic groups as well as arylalkyl amines such as benzylamine;
AA6 is selected from the group consisting of Glu, Gln, Asp, Asn, and related alpha amino acids possessing side chains containing charged or H-bond accepting groups;
AA7 is selected from the group consisting of no residue, Ala, Cys, Ser, Thr and related alpha-amino acids possessing side chains containing sufhydryl, hydroxyl groups;
AA8 is selected from the group consisting of no residue, Ile, Ala, Leu, Phe and other alpha-amino acids possessing hydrophobic side-chains, as well as arylalkyl amines such as benzylamine, phenylethylamine, phenylpropylamine, and aliphatic amines possessing short chain linear and branched alkyl groups of 1 to 8 carbons;
Z2 is attached to the carboxy-terminus of the peptide and selected from the group consisting of proton, $NH_2$, 1-3 amino acids as well as arylalkyl amines such as benzylamine, phenylethylamine, phenylpropylamine, and aliphatic amines possessing short chain linear and branched alkyl groups of 1 to 8 carbons.

It is also the aim of the invention is to provide derivatives of the said compounds which may be synthetic polypeptides, those containing conservative substitutions of individual amino acids, peptidomimetics.

Another objective is to provide compounds which are capable of modulating the functional consequences of prostaglandin E2 receptor subtype EP4 in assays using cultured cells, tissues and animals.

It is also an aim of the present invention to provide a composition comprising an antagonist of the prostaglandin E2 receptor subtype EP4 in association with a pharmaceutically acceptable carrier.

Another aim of the present invention is to provide the use of a pharmaceutical composition containing a prostaglandin E2 receptor subtype EP4 antagonist for improving glomerular filtration and/or urine output of a patient, treating end stage renal disease or acute renal failure, or closing ductus arteriosus (DA) in a premature infant patient.

Another aim of the present invention is to provide the use of a pharmaceutical composition containing a prostaglandin E2 receptor subtype EP4 antagonist for the treatment of osteoporosis.

It is another aim of the present invention to provide the use of a prostaglandin E2 receptor subtype EP4 antagonist in a bioassay and a kit that incorporates the use of the said antagonist for screening libraries of compounds.

DETAILED DESCRIPTION OF THE INVENTION

Prostanoid receptors are G protein coupled receptors whose natural ligands are the cyclooxygenase products of arachidonic acid, a C20:4 unsaturated fatty acid. No known ligands of these receptors are of peptidic in nature. Prostaglandin E2 binds many G protein-coupled receptor subtypes of which subtype EP4 is of particular importance in several pathologies. Specific antagonists of EP4 receptor are not available nor is the validation of the functional role of this receptor un mammalian physiology.

An aim of the present invention is to address such deficiencies in the arts and provide a selective inhibitor of EP4 receptor.

A novel aspect of the present invention is that the described antagonists of prostaglandin E2 receptor subtype EP4 is peptidic in nature. Also provided herein is a structure of such an antagonist and the possible derivatives which may mimic the functional and structural features of said antagonist in assays involving cells, tissues and animals, as known to people skilled in the art.

Therefore a compound is provided which comprises a peptide of at least 8 amino acid of the following general formula,

Y1-R1-R2-R3-R4-R5-R6-R7-R8-Z1 wherein,

Y1 is attached to the N-terminus of the peptide and selected from the group consisting of a proton, a sequence of 1-3 amino acids, or a blocking group such as a carbamate group, an acyl group composed of a hydrophobic moiety such as cyclohexyl, phenyl, benzyl, short chain linear and branched alkyl groups of 1-8 carbons of which acetyl and benzoyl are examples;

R1 is selected from the group consisting of Val, Ala, Ile, Gln, Leu, or Arg;

R2 is selected from the group consisting of Ala, Ile, Phe, Arg, or Leu;

R3 is selected from the group consisting of Pro, Thr, Ser, Tyr, Leu, or Val;

R4 is selected from the group consisting of Met, Ala, Gly, Ser, Val, or Ile;

R5 is selected from the group consisting of Thr, Pro, Tyr, Leu, Gly, or Gln;

R6 is selected from the group consisting of is Val, Cys, Ile, Gly, Glu, or Ser;

R7 is selected from the group consisting of is Pro, Val, Cys, Leu, Glu or Asn;

R8 is selected from the group consisting of is Ser, Leu, Thr, or Ala;

Z1 is attached to the carboxy-terminus of the peptide and selected from the group consisting of proton, $NH_2$, 1-3 amino acids as well as arylalkyl amines such as benzylamine, phenylethylamine, phenylpropylamine, and aliphatic amines possessing short chain linear and branched alkyl groups of 1 to 8 carbons.

In addition, a composition is also disclosed, wherein the composition comprises a peptide having the structure

Y2-AA1-AA2-AA3-AA4-AA5-AA6-AA7-AA8-Z2 wherein:

Y2 is attached to the N-terminus of the peptide and selected from the group consisting of a proton, a sequence of 1-3 amino acids, or a blocking group such as a carbamate group, an acyl group composed of a hydrophobic moiety such as cyclohexyl, phenyl, benzyl, short chain linear and branched alkyl groups of 1-8 carbons of which acetyl and benzoyl are examples;

AA1 is selected from the group consisting of no residue, Ile, Leu, Phe and related alpha-amino acids possessing hydrophobic side-chains, arylalkyl amines such as benzylamine;

AA2 is selected from the group consisting of no residue, Leu, Ile, Phe and related alpha-amino acids possessing hydrophobic side-chains, arylalkyl amines such as benzylamine;

AA3 is selected from the group consisting of no residue, Ala, Ser, Thr and other related alpha amino acids possessing side chains containing hydroxyl or H-bond forming groups;

AA4 is selected from the group consisting of Ser, Thr, and related alpha-amino acids possessing side chains containing hydroxyl groups or H-bond forming groups;

AA5 is selected from the group consisting of Ala, Tyr, Phe, and other related alpha amino acids possessing side chains containing benzoyl and phenolic groups as well as arylalkyl amines such as benzylamine;

AA6 is selected from the group consisting of Glu, Gln, Asp, Asn, and related alpha amino acids possessing side chains containing charged or H-bond accepting groups;

AA7 is selected from the group consisting of no residue, Ala, Cys, Ser, Thr and related alpha-amino acids possessing side chains containing sufhydryl, hydroxyl groups;

AA8 is selected from the group consisting of no residue, Ile, Ala, Leu, Phe and other alpha-amino acids possessing hydrophobic side-chains, as well as arylalkyl amines such as benzylamine, phenylethylamine, phenylpropylamine, and aliphatic amines possessing short chain linear and branched alkyl groups of 1 to 8 carbons;

Z2 is attached to the carboxy-terminus of the peptide and selected from the group consisting of proton, $NH_2$, 1-3 amino acids as well as arylalkyl amines such as benzylamine, phenylethylamine, phenylpropylamine, and aliphatic amines possessing short chain linear and branched alkyl groups of 1 to 8 carbons.

The term "amino acid" as used herein includes both L and D isomers of the naturally occurring amino acids as well as other nonproteinaceous amino acids used in peptide chemistry to prepare synthetic analogs of peptides. Examples of naturally-occurring amino acids are glycine, alanine, valine, leucine, isoleucine, serine, threonine, etc. whereas non-naturally occurring amino acids are norleucine, norvaline, cyclohexyl alanine, biphenyl alanine, homophenyl alanine, naphthyl alanine, pyridyl alanine, phenyl alanines substituted at the ortho, para and meta positions with alkoxy, halogen or nitro groups etc. These compounds are known to persons versed in the art of peptide chemistry.

The term "polar amino acid" means any amino acid containing an uncharged residue but is relatively soluble in water.

The term "hydrophobic amino acid" means any amino acid containing an uncharged side chain which is insoluble in water.

The term "patient" denotes any animal, particularly, humans.

For the purpose of clarity, commonly accepted notations of amino acids are given below:

| Full Name | Three-Letter Code | One-Letter Code |
|---|---|---|
| Aspartic Acid | Asp | D |
| Glutamic Acid | Glu | E |

-continued

| Full Name | Three-Letter Code | One-Letter Code |
|---|---|---|
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

Peptidomimetics: It is well known in the art of drug design to identify a substitute compound that mimics the conformation of the peptide, hence reproduces its functional activity, at the same time avoiding the undesirable features of peptides, such as flexibility, protease-sensitivity, oxidizability of constituents, barrier impermeability and size. Such a compound that mimics the peptide is called a "peptidomimetic". The methods of designing and synthesizing peptidomimetics are well known to people skilled in that art.

In designing peptidomimetics, people skilled in the arts analyze the structure of a given peptide by making conservative and nonconservative substitutions, deletions at each position of the amino acid and correlate such changes with alterations in physical or biological activity. For example, conservative amino acid changes may be made to the actual sequence of the peptide, which although they alter the primary sequence of the peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Further modifications include attachment of polyethylene glycol molecules of various molecular weights (PEGylation) to improve the bioavailabilty, fatty acid modification to improve its barrier penetrability, and modifications by tissue-targeting antibodies or polypeptides, small molecules are also included herein.

Also included are polypeptides which have been modified using peptide chemistry so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids, as known to persons skilled in the art of peptidomimetic chemistry.

Unless otherwise specified, all peptides and peptidomimetics used in this invention contained D-amino acids.

Furthermore, replacing blocks of amino acids with synthetic scaffolds, as practiced in case of beta turn mimetics, or use beta amino acids in place of natural amino acids are some of the practices in peptidomimetic chemistry.

Peptide synthesis: The synthesis of the peptides and peptidomimetic compounds described in this invention could be achieved by either a complete solid phase synthesis or a mixed technique whereby all or most of the peptide is synthesized by solid phase and the subsequent additions could be made in solution.

In the conventional peptide synthesis, the amino acids are sequentially coupled to achieve a complete peptide. The amino acids are conjugated to various protecting groups, such as BOC and Fmoc, hence also termed as BOC and Fmoc chemistries. The background information on peptide synthesis can be obtained by reference to "Solid phase peptide synthesis" Stewart & Young, W h Freeman Co. San Francisco, 1969 and Erikson and Merrifield, "The proteins" Vol. 2. (ed. Neurath & Hill), Academic press, New York. 1976).

In accordance with the present invention, there is provided a composition comprising an antagonist of a G protein-coupled receptor of prostaglandin $E_2$, subtype $EP_4$ in association with a pharmacologically or physiologically or pharmaceutically acceptable carrier. The choice of the carrier is denoted by the specific application for which the said antagonist is used.

Numerous pharmaceutically acceptable carriers are known in the art and can be formulated with the composition of the invention using methods known in the art.

When the composition of the invention is used in vitro, it may be suspended in any acceptable carrier, such as physiological saline or any other buffer which is compatible with the particular cell or tissue system being investigated. In vitro formulations will thus be readily apparent to the artisan skilled in the art of conducting ligand binding assays using membranes or whole cells, physiological experiments using tissues.

The activity of the compounds of the present invention could be tested in a variety of assay systems and these are documented in the literature and is known to people versed in that art. For example. Cells in which EP4 receptor is expressed naturally, such as NIH3T3, or cDNAs are exogenously expressed using recombinant expression vectors, can be used to measure the efficacy and potency of antagonism of the compounds disclosed herein. Alternately, tissues known to express EP4 receptor, for example, saphenous vein, intestinal smooth muscle etc., can be used in organ bath assays to measure contraction/dilation or the tissue fragments or the membranes derived from the tissues could be incubated with radiolabelled ligands to measure ligand displacement, GTP binding and hydrolysis, second messenger (e. g. cAMP and inositol phosphates) synthesis. All these assays involve measuring one or more of the biochemical and physiological consequences of the signal transmission from said receptor, wherein said consequences are selected from the group consisting of GTP binding and hydrolysis by $G_\alpha$ proteins, cyclic adenosine monophosphate synthesis, alterations in cell calcium, smooth muscle contraction or dilation, cell growth and/or differentiation, altered gene expression and smooth muscle contraction or dilation.

A more physiological way of assaying the activity of a compound listed herein is to introduce the compound in association with a suitable carrier in an animal using a dose range of 1 μg-1000 mg/Kg body weight and a suitable route of administration (see below). The manipulations of the animals, routes of administration and dosing regimens are known to people versed in the art. For example, the present invention contains description of the effects of certain compounds tested in rats, pigs and sheep and the methods are given in the examples.

When an antagonist of the invention is administered to a patient in need of a treatment, it may be formulated in any suitable formulation which will depend on number of factors including the particular condition to be treated, the age, the degree of disease or disorder etc. The inhibitors of the invention may be administered to a patient in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration. Formulations may also include those which render the inhibitor capable of crossing the blood brain barrier when administered by any other route. In addition, the inhibitors of the invention may be formulated so as to target specific types of cells. For example, it is now known in the art to encapsulate or otherwise formulate compounds such that they a directed to specific receptors on cells. Such formulations include antibody-tagging formulations, receptor-ligand binding formulations etc.

The inhibitors of the invention may also be administered by a peripheral route, or they may be administered systemically to the patient. "Peripheral administration" as used herein, denotes administration of a compound by any route other than direct administration to the brain. Thus, peripheral administration includes, but is not limited to, oral, nasopharyngeal, intraperitoneal, intramuscular and intravenous administration of any of the compounds of the invention.

Treatment regimes which are contemplated include a single dose or dosage which is administered hourly, daily, weekly or monthly, or yearly. Dosages may vary from 1 μg to 1000 mg/kg of body weight of the patient and will be in a form suitable for delivery of the compound. The route of administration may also vary depending upon the disorder to be treated.

In accordance with the above description, use of a pharmacological composition containing an EP4 antagonist in situations wherein administraion of such a composition to a patient having a therapeutic need, results in increment in glomerular filtration and urine output. It is also envisaged that said formulation may be given to patients diagnosed with acute renal failure or end stage renal disease or a variety of glomerulopathies or nephropathies.

It is also mentioned that a pharmaceutical composition containing an antagonist of EP4 receptor may be administered to a patient or animal diagnosed with bone mineral loss, as seen in conditions of osteoporosis or dental disease or many immune and cancer-related diseases.

The use of a pharmaceutical preparation containing EP4 antagonist is also included in the present invention where a need to close the patent ductus arteriosus to avoid pulmonary hypertension in a premature infant.

The dose of an EP4 antagonist may be 1 μg-1 g/Kg of body weight of the patient or animal and administered by a peripheral route.

Another embodiment of the invention is that the peptide antagonists described in this invention could be used as a tool to validate the novel roles of prostaglandin E2 receptor subtype EP4 in tissues or in whole animals. For example, though $EP_4$ receptor is known to be present in glomerulus (Breyer, M. D., 1998; Morath, R., 1999) and ductus arteriosus (Bhattacharya, M. et al., 1999), the precise function of the receptor in these structures and in the physiology of the animal is not known. As described in the invention by using specific antagonists, inhibition of $EP_4$ receptor is shown to increase glomerular filtration and urine output in rats, close the ductus arteriosus in fetal sheep and decrease osteoclasogenesis in human spleen cell co-cultures with osteoblasts. By providing such specific antagonists of the receptor with or without the knowledge of the natural ligand, persons versed in the art, can study the novel roles of prostaglandin E2 receptor subtype EP4 or other G protein-coupled receptors in tissues as well as in whole animals.

Another embodiment of the present invention is the use of the antagonist of EP4 receptor in a biochemical assay to validate the function of unknown ligands, physically identify and localize the said receptor in cells and tissues using such techniques as autoradiography, radioligand binding, radioscintigraphy, positron emmision tomography etc. and the specific techniques vary with the experimental subject and are well known to the persons skilled in such an art. Therefore, a kit containing the antagonist of EP4 receptor attached with various labels, such as fluorochromes, radionucleides, immunoaffinity haptens, antibodies and other affinity tags, is also included in the present invention.

Preparation of Inhibitors and Materials

Chemical Synthesis of Peptides and Peptidomimetics:

We have synthesized using F-moc chemistry and solid phase Merrifield method several peptides and peptidomimetics. The purity of these peptides was assessed by HPLC and mass spectroscopy. The general methods are understood by referring to the following treatises: "Solid phase peptide synthesis" Stewart & Young, W h Freeman Co. San Francisco, 1969 and Erikson and Merrifield, "The proteins" Vol. 2. (ed. Neurath & Hill), Academic press, New York. 1976).

Unless otherwise specified, all peptides and peptidomimetics contained D-amino acids. For in vitro experiments, peptides were weighed and dissolved in dimethyl sulfoxide at 10 mM and for in vivo experiments, in sterile saline at the indicated concentrations. The solutions were made freshly and discarded after use.

Expression of $EP_4$ cDNA in HEK 293 cells:

Human $EP_4$ coding region was amplified from Jurkat cells. using RT-PCR. Briefly, total RNA was extracted from Jurkat cells (~$10^7$ cells) using the Trizol™ reagent (Life technologies, Burlington, ON). The purity and the quantity of the RNA were assessed by determining the absorption at 260 and 280 nm. An aliquot of the RNA was reverse transcribed using Superscript II reverse transcriptase (Life technologies, Burlington, ON) (200 U) and 100 μM oligo(dT)$_{12-18}$ in the reaction buffer (50 mM Tris-HCl pH 8.3, 75 mM KCl, 3 mM $MgCl_2$, 10 mM DTT) for 1 h at 42° C. A portion of the cDNA (corresponding to 1 μg of RNA) was amplified by PCR using 10 μM each of primers, EP4.1 (5' ATC ATG TCC ACT TCC GGG GTC 3' SEQ ID NO: 10) and EP4.2 (5' CTA TTA TAT ACA TTT TTC TGA TAA GTT CAG 3' SEQ ID NO: 11) and 2 U Vent™ polymerase (New England Biolabs, Mississauga, ON) in Thermopol™ (New England Biolabs, Mississauga, ON) reaction buffer (20 mM Tris-HCl pH 8.8, 10 mM KCl, 10 mM $(NH_4)_2SO_4$, 2 mM $MgSO_4$, 0.1% Triton X-100, 0.2 mM dNTPs and 5% DMSO) for 30 cycles (94° C.-1 min; 55° C.-1 min; 72° C.-1.5 min). The DNA fragment was purified by agarose gel electrophoresis, phosphorylated by T4 polynucleotide kinase and cloned into Hinc II site of pGEM-3 (Promega, Madison, Wis.) by blunt-end ligation using standard molecular biology methods (Maniatis, T. et al. 1989. *Molecular cloning: a laboratory manual*. Cold Spring Harbor Press. New York). The sequence of the $EP_4$ cDNA was determined by sequencing. $EP_4$ coding region (Hind III-Xba I fragment) was cloned into a eukaryotic expression vector, pRC-CMV (Invitrogen, San Diego, Calif.) to give EP4/RC-CMV plasmid.

HEK293 cells ($2\times10^5$ cells/well of a 6-well plate) were transfected with EP4/RC-CMV using lipofectamine™ (Life technologies, Burlington, ON) according to the instructions supplied by the manufacturer. Briefly, 2 µg of plasmid was complexed with 4 µl of lipid in OPTI-MEM medium for 30 min and the DNA-lipid complexes were added to the cells and left for 6 h at 37° C. Later, the medium was replaced with DMEM containing 10% FBS. After two days, the cells were split into DMEM medium and the antibiotic-resistant cells were selected with 1 mg/ml G418 (Life technologies, Burlington, ON). After 10-12 days in selection, G418-resistant colonies were pooled and propagated. $EP_4$ receptor expression in the pooled population of cells was confirmed by radioligand binding and cAMP synthesis in response to $PGE_2$.

The present invention will be more readily understood by referring to the following examples which are given to illustrate the invention rather than to limit its scope.

EXAMPLE I

Basal and $PGE_2$-stimulated Cyclic Adenosine Monophosphate Levels in Response to PHG 213

Basal cAMP levels in $EP_4/293$ cells were increased compared to the parent HEK293 cells in the presence of isobutyl methylxanthine (IBMX), a phosphodiesterase inhibitor; this is attributed mainly to the increased basal activity of adenylate cylcase due to the over-expression of $EP_4$ receptor. The efficacy of the peptide inhibitors was tested on the basal levels of cAMP in these cells.

Method: $EP_4/293$ cells were seeded at $5\times10^5$ cells/well in 6-well plates and next day, treated with 100 µM of IBMX for 1 h in the presence or absence of PHG213 (100 µM). The medium was removed and 0.3 ml of ethanol was added to precipitate the protein and extract cAMP. Protein-free supernatants obtained after centrifugation were lyophilized. The residues were resuspended in binding buffer and the cAMP levels were determined using a commercial kit.

The results are presented in Table 1 below. The cells were treated with PHG213 (SEQ ID NO:1) (100 µM) in the presence of 100 µM IBMX for 1 h. Forskolin and $PGE_2$ were added for only 15 min. Data are averages of four replicates. Table 1 illustrates the alterations in basal and $PGE_2$-stimulated cyclic adenosine monophosphate levels in response to PHG 213.

TABLE 1

Effect of PHG213 on basal cAMP levels in $EP_4/293$ cells

| peptide | CAMP (pmol/ml/$10^5$ cells) | % inhibition |
|---|---|---|
| vehicle | 69.9 | — |
| PHG 213 | 27.5 | 60.7 |
| $PGE_2$ (1 µM) | >270 | — |
| FSK (100 µM) | >270 | — |

Basal cAMP levels increased over time in the presence of IBMX in $EP_4/293$ cells. PHG213 potently decreased the accumulation of cAMP. Addition of PGE2 (1 µM) or forskolin (100 µM), an adenylate cylcase activator, increased cAMP levels suggesting that the $EP_4$ signaling pathway consisting of adenylate cyclase was fully active in these cells. Thus it appeared that PHG213 is a potent inhibitor of basal activity of $EP_4$ receptor in these cells.

EXAMPLE II

Effects of PHG213 and its Peptidomimetic Variants on PGE2-induced Dilation of Saphenous Vein Strips in Organ Bath Assay In order to produce a potent antagonist, various modifications of the sequence of 213 (SEQ ID NO:1) were designed and synthesized using F-moc chemistry. Peptides and peptidomimetics were purified using HPLC. These include 213.2: (SEQ ID NO:2); 213.4: (SEQ ID NO:3); 213.6: (SEQ ID NO:4); 213.7: (SEQ ID NO:5); 213.9: (SEQ ID NO:6); 213.15: (SEQ ID NO:7); 213.16: (SEQ ID NO:8); 213.17: (SEQ ID NO:9).

Animals. Yorkshire piglets (2-4 days old) were used in this study, according to a protocol approved by the Animal Care Committee of the Research Centre of Ste-Justine Hospital. Briefly, animals were anesthetized with 1.5% halothane and the lower external saphenous veins removed and placed in cold Krebs buffer (pH 7.4) of the following composition (mM): NaCl 120, KCl 4.5, $CaCl_2$ 2.5, $MgSO_4$ 1.0, $NaHCO_3$ 27, $KH_2PO_4$ 1.0, glucose 10, to which 1.5 U/ml heparin was added.

Organ bath assay. The saphenous veins were cleaned of extraneous tissue and cut into 4 mm rings that were placed in individual jacketed organ baths (15 ml; Radnoti Glass, Monrovia, Calif.) containing Krebs buffer and maintained at 37° C. The solution was bubbled with a mixture of 95% $O_2$-5% $CO_2$. In each experiment, 8 rings were used (4 from each saphenous vein) and were equilibrated for 60 min under 2.0 gr passive tension, with frequent washing and tension adjustment. Tension was measured by force-displacement transducers and was recorded on a computerized data acquisition system using the Work Bench software (both from Kent Scientific, Litchfield, Conn.).

Experimental protocol. In a first set of experiments, the relative distribution of dilatory EP receptor subtypes was ascertained using a combination of EP receptor agonists and antagonists. The vasodilatory response of the lower external saphenous veins to $PGE_2$ appears to result from the stimulation of 30% $EP_2$ and 70% $EP_4$. Tissues were initially challenged with $2\times10^{-7}$ U46619 which induced a 1.5 to 2.0 gr increase in tension. Rings which did not respond were discarded. When the response to U46619 reached a steady state, agents were added. When no response to the agents were observed, a period of 10 minutes was allowed to insure proper distribution of the agents in the tissue. Dose-response curves to PGE$_2$ ($10^{-10}$–$10^{-6}$ M) were then obtained in the presence of absence of each of the tested drugs.

The results of the experiments were shown in Table II below. The results are average of 2-8 experiments. The results are tabulated as percent reversal of 1 μM PGE2-induced constriction in the presence of 1 μM peptides. The peptides shown here contain productive and effective substitutions in the parent peptide PHG 213 (SEQ ID NO:1)

TABLE 2

Effects of peptidomimetic derivatives of PHG213 on PGE2-induced vasorelaxation in saphenous vein of piglet

| SEQ ID NO | % blockade of PGE2 induced vasodilation |
|---|---|
| 1 | 50.0 |
| 2 | 35.0 |
| 3 | 20.0 |
| 4 | 60.0 |
| 5 | 60.0 |
| 6 | 30.0 |
| 7 | 65.5 |
| 8 | 64.5 |
| 9 | 34.0 |

EXAMPLE III

Effects of PHG213 on Ocular Perfusion Rates in Porcine Eye Model

In order to test the efficacy of PHG213 (SEQ ID NO: 1) on EP$_4$ receptor function, an ex vivo assay of vasomotricity of porcine choroid was used. The dilatory response to PGE$_2$ in this vascular bed was previously shoen to be mediated by EP$_4$ receptor (Abran, D. et al. 1997. *Am. J. Physiol.* 272: R995-1001).

Method: The method as described in detail by Abran et al. (1997) was followed exactly. A vortex vein from the eye of a newborn pig was catheterized with a 27-gauge needle and perfused with Kreb's solution until perfusion pressure was stable. The vasculature was first constricted with a thromboxane mimetic, U46619 (1 μM), and then PGE$_2$ was infused at 1 μM. Once the reversal of constriction reached a plateau, then PHG213 was infused at 100 μM and the perfusion pressure was recorded.

Figure 1:
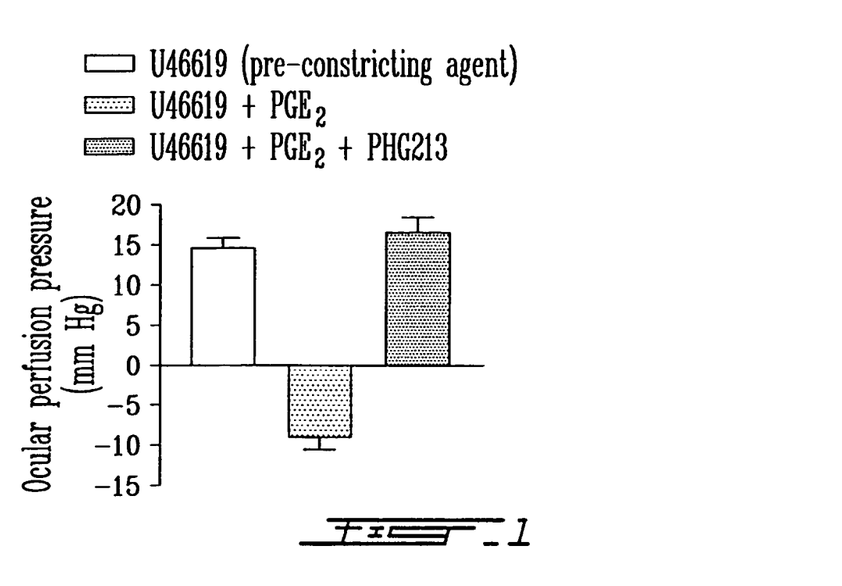
FIG. 1 illustrates the effects of PHG213 on the changes in ocular perfusion pressure in response to $PGE_2$.

The results are shown in FIG. 1. Positive values of perfusion pressure indicate constriction whereas negative values indicate dilation of the vasculature. PGE$_2$ reversed the constriction produced by U46619. Perfusion of PHG213 blocked this dilatory effect of PGE$_2$ completely. Since it is known that the dilatory effects of PGE$_2$ are predominantly mediated by EP$_4$ receptor in choroid of the newborn pig, PHG 213 antagonized the actions of EP$_4$ receptor and blocked the dilation produced by this receptor.

EXAMPLE IV

Effects of PHG213 on Glomerular Filtration Rate and Urinary Volume in Normal Rats EP$_4$ receptor is localized in glomerulus and possibly, in the collecting duct and we hypothesized that EP$_4$ antagonist may increase glomerular filtration rate. For this purpose, we have developed and tested PHG 213 (SEQ ID NO:1) in an in vivo rat model.

Method: Sprague-Dawley adult rats (~250 g) were anesthetized with 50 mg/kg pentobarbitone. Left jugular vein (for infusion) and left carotid artery (for measuring blood pressure) were catheterized and another catheter was placed at the tip of the bladder for collecting urine. Infusion of [$^3$H]-inulin in saline (2 μCi/Kg/h) was started and continued for 2 h to stabilize the system. Urine collection was exactly for 20 min and at 10 min mark, 0.1 ml of blood was withdrawn into heparinized tubes. Blood was centrifuged and radioactivity in plasma was counted. After 10 min and 30 min (30 min and 60 min since the start of the previous urine collection), the process was repeated. The antagonist, PHG 213, was infused in saline i.v. at 6 μmol/Kg/h for one hour before the start of first urine collection. Urinary volume (UV) is calculated and expressed as μl of urine/h corrected for the weight of the animal. GFR was calculated as the ratio of urinary insulin concentration to plasma insulin concentration corrected for the volume of the urine and the weight of the animal.

Figure 2:
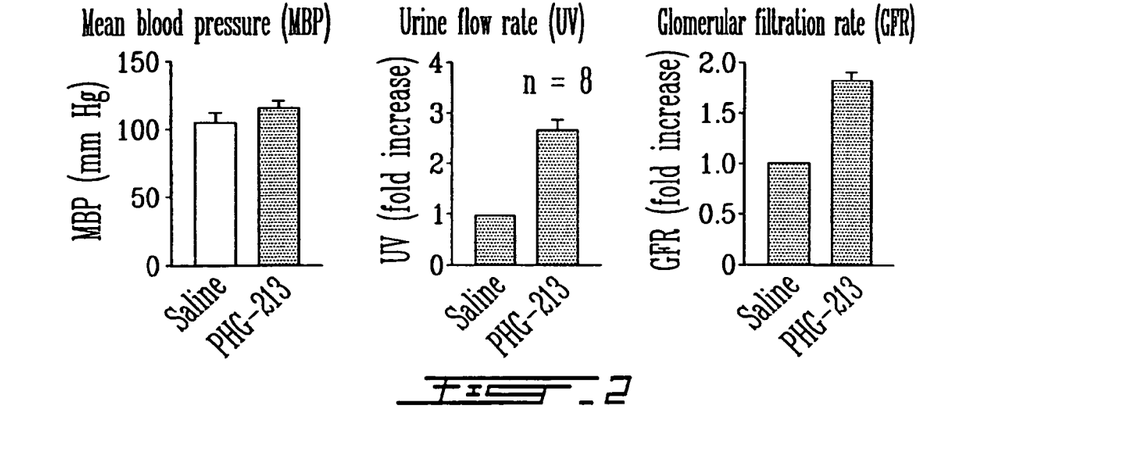
FIG. 2 illustrates the effects of PHG213 on glomerular filtration rate and urinary volume in normal rats.

The results are shown in FIG. 2. The mean blood pressure was not significantly altered by the peptide. Urinary flow rate (UV) dramatically increased by 2.3 fold and glomerular filtration rate(GFR) increased by 157%. These alterations in urine output are indications of the EP$_4$ receptor antagonist effects in the glomerulus where it increased filtration and in the collecting duct where it inhibited re-absorption, thus resulting in higher urine output.

EXAMPLE V

Effects of PHG213 on Glomerular Filtration Rate and Urinary Volume in Diabetic Rats Decreased glomerular function is a hallmark of end-stage renal disease (ESRD) and drugs that improve GFR will be of immense therapeutic value in delaying the progression of the disease. In order to find if EP$_4$ antagonists could increase glomerular function, we have used the streptozotocin-induced diabetic rat as a model.

Method: Sprague-Dawley adult rats (~250 g) were injected i.p. with streptozotocin (45-50 mg/Kg) and two days later, the urine was tested for glucose and proteinuria. Two weeks later, the rats that tested positive for both markers were chosen to test the effects of PHG 213 (SEQ ID NO:1) on GFR and UV using a method described above.

Figure 3:
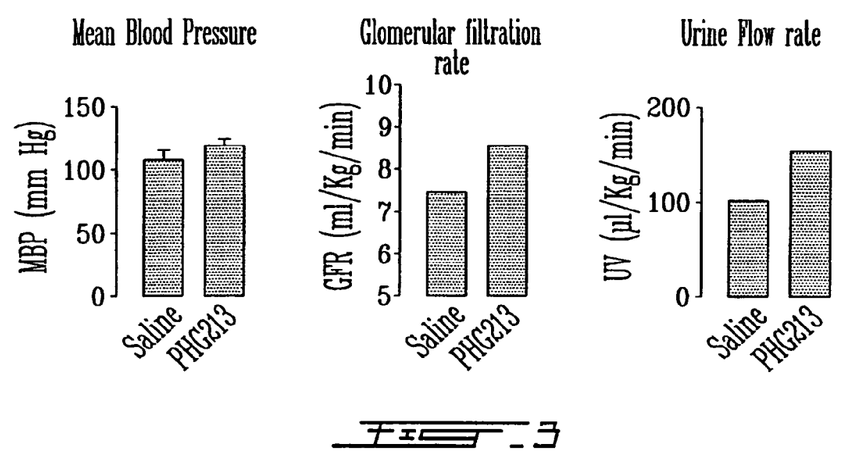
FIG. 3 illustrates the effects of PHG213 on glomerular filtration rate and urinary volume in diabetic rats.

The results are shown in FIG. 3. Systemic infusion of EP4.3 increased, in accordance with its postulated inhibition of PGE$_2$ effects via EP$_4$ receptor, both GFR and UV. Mean blood pressure was not significantly altered in these animals, suggesting that EP$_4$ receptor contributes minimally to blood pressure homeostasis which is a desirable attribute of the drug. These results suggest that in diabetic animals similar to the non-diabetic animals, EP$_4$ receptor is expressed and regulates glomerular filtration.

EXAMPLE VI

Effects of PHG213 on the Ductus Arteriosus of Fetal Sheep

Pregnant ewes (129-140 days of gestation) was anesthetized with ketamine (30 mg/Kg i.v.), a caesarian section was performed and the fetus exteriorized. To mimic fetal respiratory conditions, the head of the fetus was submerged in a glove filled with saline. Femoral and jugular veins were catheterized for systemic blood pressure measurements and drug infusions respectively. Ductus arteriosus (DA) diameter was measured using Doppler echocardiography as described before (Teyssier, G. et al. 1989. *J. Cardiovascular Technol.* 8: 259-266). Echocardiographic measurements were performed with an Acuson 128 XP/10C real time ultrasound imaging system using 7.5 or 5-MHz transducers duplexed with a range-gated Doppler. Doppler signals were filtered by a 100-Hz high-pass filter. The DA was visualized through a left second intercostal parasternal approach. After the drugs were injected, measurements of DA diameter were repeated 3 times at 5 min intervals for the next 20-25 min.

Figure 4:
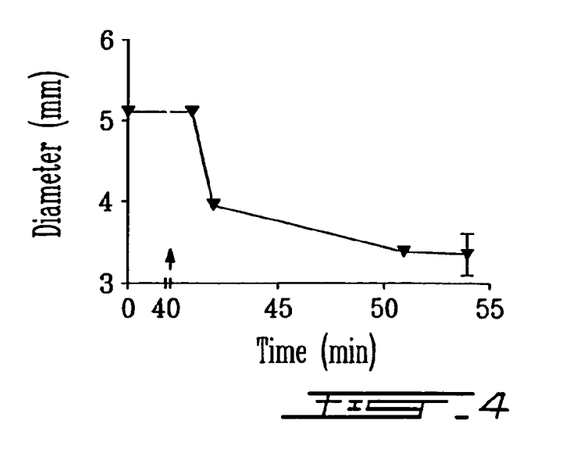
FIG. 4 illustrates the effects of PHG 213 on ductus arteriosus diameter in fetal sheep measured by Doppler-echocardiography.

The results are shown in FIG. 4. DA was unchanged for 40 min during the stabilization period. Within minutes following infusion of PHG213 (SEQ ID NO:1) (2 mg of bolus followed by 1 mg/Kg infusion over 15 min), DA started to constrict and continued for another 15 min and was irreversible. PHG213, a peptide antagonist of EP4 receptor, blocked the dilatory action of the receptor which is responsible for maintaining the ductus open in the fetus.

EXAMPLE VII

Effects of PHG213 on Osteoclasogenesis in Cocultures of Human Spleen Cells and SaOS-2 Immortalized and Fixed Human Osteoblasts Osteoclasts attach to bone and cause resorption or bone loss. It is therapeutically advantageous to inhibit the increment in the number of osteoclasts (osteoclast differention) in osteoporosis in order to prevent the bone loss. In order to test the efficacy of PHG213 (SEQ ID NO 1) on osteoclast differentiation, a coculture system of human fetal spleen cells and human osteoblast cells was used.

Method: SaOs-2 cells (immortalized cell line of human osteoblasts) were grown for four days in 24-well plates in alpha-MEM medium containing 10% fetal calf serum, vitamin D3 ($10^{-7}$). Confluent SaOs-2 cells were fixed in 1% paraformaldehyde M) and dexamethasone ($10^{-8}$ M in phosphate-buffered sline (PBS) for 8 min. The cells were rinsed with PBS 4 times and alpha-MEM containing 10% fetal calf serum and vitamin D3 ($10^{-7}$ M) was added.

Two days before, spleens from human abortuses were cut into small pieces and triturated several times release the cells. The spleen cells were cultured in alpha-MEM containing 10% fetal calf serum for 2 days. Spleen cells were trypsinized, rinsed once in PBS and counted using a coulter counter. An aliquot of spleen cells ($10^5$ cells/well) were placed over the monolayer of fixed SaOs-2 cells for 2 h, after which PHG213 (100 μM) was added. Three days later, the cells were fixed in 4% paraformaldehyde in PBS, rinsed with water and tartarat-resistant alkaline phosphatase (TRAP) was stained using a commercial kit (Sigma, St. Louis, Mo.). TRAP-positive cells were viewed under a microscope and counted.

Figure 5:
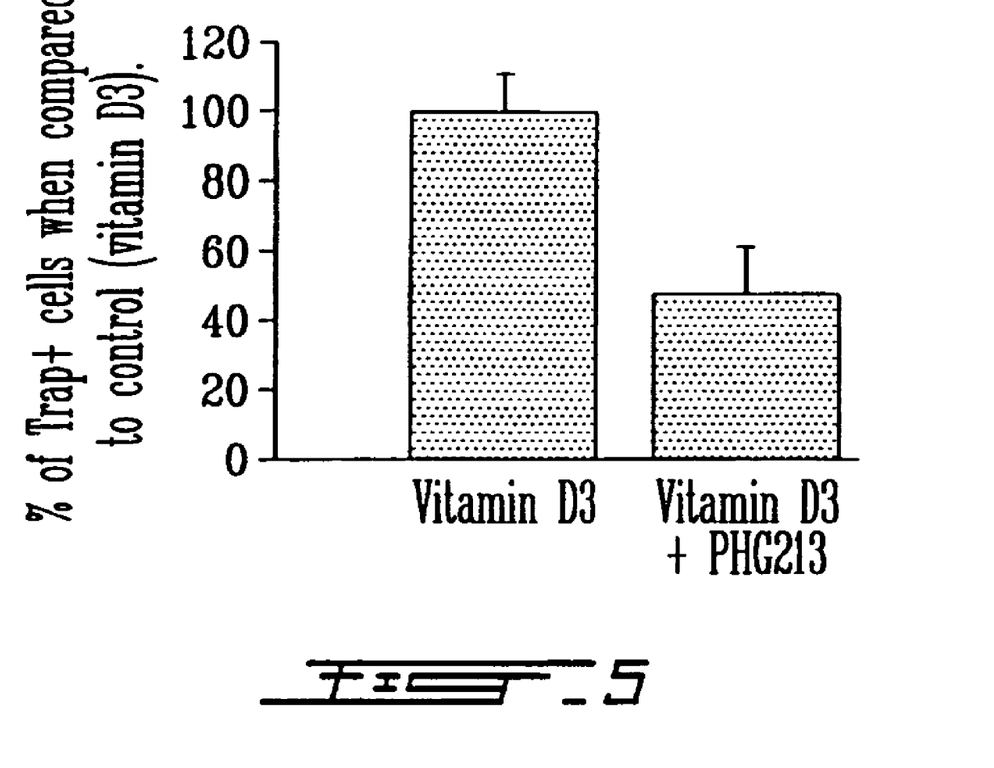
FIG. 5 illustrates the effect of PHG213 on osteoclastogenesis (TRAP+cells) with human fetal spleen cells in coculture with fixed SaOS-2 cells.

The results of the experiments were shown FIG. 5. Data are average of several experiments (n=10). Addition of PHG213 reduced the number of TRAP-positive cells (osteoclasts) by half in this human cell coculture system. This is the first time that a specific inhibitor of human EP4 receptor, PHG213, prevented the differentiation of progenitor cells in spleen to become osteoclasts, thus the inhibition of EP4 receptor has potential application in treating osteoporosis which is characterized by excess bone loss mediated by osteoclasts.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated peptide, wherein said peptide consists of an amino acid sequence selected from the group consisting of IFTSYECL (SEQ ID NO: 1); IFASYECL (SEQ ID NO: 2); IFTSAECL (SEQ ID NO: 3); IFTSYEAL (SEQ ID NO: 4); ILASYECL (SEQ ID NO: 5); IFTSYDCL (SEQ ID NO: 6); (4-biphenyl alanine) TSYEAL (SEQ ID NO: 7); (diphenyl alanine) TSYEAL (SEQ ID NO: 8); and (homophenyl alanine) TSYEAL (SEQ ID NO: 9).

2. A pharmaceutical composition containing the peptide of claim 1 in association with a suitable pharmaceutical carrier.

3. A method of improving glomerular filtration and/or urine output of a patient comprising the step of administering to said patient in need of such a treatment a therapeutically effective amount of a peptide of SEQ ID NO: 1.

4. The peptide of claim 1, wherein said peptide comprises one or more D-amino acids.

5. The peptide of claim 1, wherein said peptide comprises all D-amino acids.

* * * * *

```
SEQUENCE LISTING

<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: Peptide inhibitor of prostaglandin E2 receptor
      subtype EP4

<400> SEQUENCE: 1

Ile Phe Thr Ser Tyr Glu Cys Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Peptide inhibitor of prostaglandin E2 receptor
      subtype EP4

<400> SEQUENCE: 2

Ile Phe Ala Ser Tyr Glu Cys Leu
1               5

<210> SEQ ID NO 3
<211> LENGTH: 8
```

```
<212> TYPE: PRT
<213> ORGANISM: Artificial Sequence
<220> FEATURE:
<223> OTHER INFORMATION: Peptide inhibitor of prostaglandin E2 receptor
      subtype EP4

<400> SEQUENCE: 3

Ile Phe Thr Ser Ala Glu Cys Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Peptide inhibitor of prostaglandin E2 receptor
      subtype EP4

<400> SEQUENCE: 4

Ile Phe Thr Ser Tyr Glu Ala Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Peptide inhibitor of prostaglandin E2 receptor
      subtype EP4

<400> SEQUENCE: 5

Ile Leu Ala Ser Tyr Glu Cys Leu
1               5

<210> SEQ ID NO 6
<211> LENGTH: 8
<212> TYPE: PRT
<213> ORGANISM: Artificial Sequence
<220> FEATURE:
<223> OTHER INFORMATION: Peptide inhibitor of prostaglandin E2 receptor
      subtype EP4

<400> SEQUENCE: 6

Ile Phe Thr Ser Tyr Asp Cys Leu
1               5

<210> SEQ ID NO 7
<211> LENGTH: 7
<212> TYPE: PRT
<213> ORGANISM: Artificial Sequence
<220> FEATURE:
<223> OTHER INFORMATION: Peptide inhibitor of prostaglandin E2 receptor
      subtype EP4
<220> FEATURE:
<221> NAME/KEY: MOD_RES
<222> LOCATION: (1)...(1)
<223> OTHER INFORMATION: 4-biphenyl alanine

<400> SEQUENCE: 7

Xaa Thr Ser Tyr Glu Ala Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Peptide inhibitor of prostaglandin E2 receptor
      subtype EP4
```

```
<220> FEATURE:
<221> NAME/KEY: MOD_RES
<222> LOCATION: (1)...(1)
<223> OTHER INFORMATION: Diphenyl alanine

<400> SEQUENCE: 8

Xaa Thr Ser Tyr Glu Ala Leu
 1               5

<210> SEQ ID NO 9
<211> LENGTH: 7
<212> TYPE: PRT
<213> ORGANISM: Artificial Sequence
<220> FEATURE:
<223> OTHER INFORMATION: Peptide inhibitor of prostaglandin E2 receptor
      subtype EP4
<220> FEATURE:
<221> NAME/KEY: MOD_RES
<222> LOCATION: (1)...(1)
<223> OTHER INFORMATION: Homophenyl alanine

<400> SEQUENCE: 9

Xaa Thr Ser Tyr Glu Ala Leu
 1               5

<210> SEQ ID NO 10
<211> LENGTH: 21
<212> TYPE: DNA
<213> ORGANISM: Artificial Sequence
<220> FEATURE:
<223> OTHER INFORMATION: cDNA primer

<400> SEQUENCE: 10
atcatgtcca cttccggggt c                                           21

<210> SEQ ID NO 11
<211> LENGTH: 30
<212> TYPE: DNA
<213> ORGANISM: Artificial Sequence
<220> FEATURE:
<223> OTHER INFORMATION: cDNA primer

<400> SEQUENCE: 11
ctattatata catttttctg ataagttcag                                  30
```